US006218383B1

(12) United States Patent
Bencherif

(10) Patent No.: US 6,218,383 B1
(45) Date of Patent: Apr. 17, 2001

(54) PHARMACEUTICAL COMPOSITIONS FOR THE PREVENTION AND TREATMENT OF CENTRAL NERVOUS SYSTEM DISORDERS

(75) Inventor: Merouane Bencherif, Winston-Salem, NC (US)

(73) Assignee: Targacept, Inc., Winston-Salem, NC (US)

(*) Notice: Subject to any disclaimer, the term of this patent is extended or adjusted under 35 U.S.C. 154(b) by 0 days.

(21) Appl. No.: 09/130,498

(22) Filed: Aug. 7, 1998

(51) Int. Cl.$^7$ .................................................. A61K 31/55
(52) U.S. Cl. .................. 514/214.01; 514/215; 514/290; 514/343
(58) Field of Search .............................. 514/214.01, 215, 514/290, 343

(56) References Cited

U.S. PATENT DOCUMENTS

| | | | |
|---|---|---|---|
| 4,965,074 | * 10/1990 | Leeson | 424/449 |
| 5,212,188 | 5/1993 | Caldwell et al. | 514/343 |
| 5,242,916 | * 9/1993 | Lippiello et al. | 514/214 |
| 5,434,170 | 7/1995 | Andrulis, Jr. | 514/323 |
| 5,466,696 | 11/1995 | Woolf | 514/297 |
| 5,576,022 | * 11/1996 | Yang et al. | 424/472 |
| 5,597,919 | 1/1997 | Dull et al. | 544/242 |
| 5,616,716 | 4/1997 | Dull et al. | 546/300 |
| 5,726,316 | 3/1998 | Crooks et al. | 546/311 |

FOREIGN PATENT DOCUMENTS

WO96/31475  10/1996  (WO).

OTHER PUBLICATIONS

JICST AN: 97A0766407, Giacobini, Jpn. J. Pharmacol., 1997, vol.74, No. 3, 225–241 (abstract).*
Medline AN: 88154340, Flood, Journla of Gerontology, (Mar. 1988), 43(2), B54–6 (abstract).*
Conway, *Clinical Neuropharmacology,* vol. 21(1), p. 8–17 (1998).
Samuels et al., *Drug Safety,* vol. 16(1), p. 66–77 (1997).
Samuels et al., *Harvard Rev. Psychiatry,* vol. 6(1), p. 11–22 (1998).
Benzi et al.,*European Journal of Pharmacology,*vol. 346(1), p. 1–13 (1998).
Capone, *Mental Retardation and Developmental Disabilities Research Reviews,* vol. 4(1), p. 36–49 (1998).
Chatellier et al., *BMJ,* vol. 300, p. 495–499 (1990).
Knapp et al., *JAMA,* vol. 217, p. 985–991 (1994).
Nordberg et al., *Alzheimer Disease and Associated Disorders,* vol. 12 (3), p. 228–237 (1998).
Bencherif et al., *JPET,* 279:1413 (1996).
Lippiello et al., *JPET,* 279:1422 (1996).
Currau et al., *Primary Care Psychiatry,* vol. ¾, p. 151–162 (1997).
R. Nikolov, Alzheimer's Disease Therapy—an Update; Highlights of the 5$^{th}$ International Geneva/Springfield Symposium on Advances in Alzheimer Therapy held in Geneva, Switzerland, Apr. 15–18, 1998, *Drug News Perspect,* 11(4), May 1998.
International Search Report; Jan. 11, 1999; F.J. Reynolds Tobacco Company et at.; PCT/US99/12243.

* cited by examiner

*Primary Examiner*—Dwayne C. Jones
*Assistant Examiner*—C. Delacroix-Muirheid
(74) *Attorney, Agent, or Firm*—Myers Bigel Sibley & Sajovec, P.A.

(57) ABSTRACT

A pharmaceutical composition incorporates a pharmaceutically effective amount of at least two components, one of those components being a nicotinic compound capable of interacting with nicotinic cholinergic receptors (e.g., a nicotinic agonist, such as E-metanicotine) and one of those components being an acetylcholinesterase inhibitor (e.g., tacrine). The pharmaceutical composition is useful for treating CNS disorders, such as Alzheimer's disease.

10 Claims, No Drawings

PHARMACEUTICAL COMPOSITIONS FOR THE PREVENTION AND TREATMENT OF CENTRAL NERVOUS SYSTEM DISORDERS

BACKGROUND OF THE INVENTION

The present invention relates to pharmaceutical compositions, and particularly pharmaceutical compositions incorporating compounds that are capable of affecting acetylcholine levels. More particularly, the present invention relates to pharmaceutical compositions incorporating at least one component capable of inhibiting acetylcholinesterase and at least one compound capable of interacting with (e.g., activating) nicotinic cholinergic receptors (e.g., at least one agonist of specific nicotinic receptor subtypes). The present invention also relates to methods for treating a wide variety of conditions and disorders, and particularly conditions and disorders associated with dysfunction of the central and autonomic nervous systems.

Central nervous system (CNS) disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type), Parkinsonism including Parkinson's disease, Lewy body diseasse (LBD), supranuclear palsy (SNP), Huntington's chorea, tardive dyskinesia, hyperkinesia, mania, attention deficit disorder, anxiety, dyslexia, schizophrenia and Tourette's syndrome.

Nicotine has been proposed to have a number of pharmacological effects. See, for example, Pullan et al. *N. Engl. J. Med.* 330:811–815 (1994). Certain of those effects may be related to effects upon neurotransmitter release. See for example, Sjak-shie et al., *Brain Res.* 624:295 (1993), where neuroprotective effects of nicotine are proposed. Release of acetylcholine and dopamine by neurons upon administration of nicotine has been reported by Rowell et al., *J. Neurochem.* 43:1593 (1984); Rapier et al., *J. Neurochem.* 50:1123 (1988); Sandor et al., *Brain Res.* 567:313 (1991) and Vizi, *Br. J. Pharmacol.* 47:765 (1973). Release of norepinephrine by neurons upon administration of nicotine has been reported by Hall et al., *Biochem. Pharmacol.* 21:1829 (1972). Release of serotonin by neurons upon administration of nicotine has been reported by Hery et al., *Arch. Int. Pharmacodyn. Ther.* 296:91 (1977). Release of glutamate by neurons upon administration of nicotine has been reported by Toth et al., *Neurochem Res.* 17:265 (1992). In addition, nicotine reportedly potentiates the pharmacological behavior of certain pharmaceutical compositions used for the treatment of certain disorders. See, Sanberg et al., *Pharmacol. Biochem. & Behavior* 46:303 (1993); Harsing et al., *J. Neurochem.* 59:48 (1993) and Hughes, *Proceedings from Intl. Symp. Nic.* S40 (1994). Furthermore, various other beneficial pharmacological effects of nicotine have been proposed. See, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., *JPET* 221: 91–96 (1982) and Hamon, *Trends in Pharmacol. Res.* 15:36.

Various nicotinic compounds have been reported as being useful for treating a variety of conditions and disorders, including various CNS disorders. See, for example, Williams et al. *DN&P* 7(4):205–227 (1994), Americ et al., *CNS Drug Rev.* 1(1):1–26 (1995), Americ et al., *Exp. Opin. Invest. Drugs* 5(1):79–100 (1996), Bencherif et al., *JPET* 279:1413 (1996), Lippiello et al., *JPET* 279:1422 (1996), Damaj et al., *Neuroscience* (1997), Lin et al., *J. Med. Chem.* 40: 385–390 (1997), Holladay et al., *J. Med. Chem* 40(28): 4169–4194 (1997), Bannon et al., *Science* 279: 77–80 (1998), PCT WO 94/08992, PCT WO 96/31475, and U.S. Pat. No. 5,583,140 to Bencherif et al., U.S. Pat. No. 5,597, 919 to Dull et al., U.S. Pat. No. 5,604,231 to Smith et al. and U.S. Pat. No. 5,616,716 to Dull et al.

Various acetylcholinesterase (AChE) inhibitors have been reported as being useful for treating a variety of conditions and disorders, including various CNS disorders. AChE inhibitors limit the activity of the enzyme, acetylcholinesterase, which hydrolyzes the endogenous neurotransmitter acetylcholine (ACh); and as such, AChE inhibitors reportedly preserve existing ACh levels in patients treated therewith, and the resulting increase in extracellular ACh within the CNS reportedly restores central cholinergic hypofunction and hence improves memory and cognition. One commercially available AChE inhibitor Cognex, which is marketed as a treatment for Alzheimer's disease as capsule containing tacrine hydrochloride, available from Parke-Davis Division of Warner-Lambert Company. Another-commercially available AChE inhibitor is Aricept, which is a capsule containing donezepil hydrochloride, available from Eisai. Other reported AChE inhibitors include Amirine from Nikken Pharmaceuticals, SW-10888 from Sumitomo, MF-217 from Mediolanum Pharmaceutici-Angelini, Ro 45-5934, HP-290 from Hoesht-Russel, ENA 713 from Sandoz, Itameline from Hoesht, Metrifonate from Bayer-Wiles, Tak 177 from Takeda, CP 118.954 from Pfizer, Galanthamine from Naedheim Pharmaceuticals, ONO 1603 from Ono, Zifrosilone from Marion Merrel Dow. See, for example those AChE inhibitors set forth in Brufani et al, *Alzheimer Disease: From Molecular Biology to Therapy,* eds. Becker et al., pp. 171–177 (1996); Schmidt et al., *Alzheimer Disease: From Molecular Biology to Therapy,* eds. Becker et al., pp. 217–221 (1996); Vargas et al., *Alzheimer Disease: From Molecular Biology to Therapy,* eds. Becker et al., pp. 251–255 (1996); Greig et al., *Alzheimer Disease: From Molecular Biology to Therapy,* eds. Becker et al., pp. 231–237 (1996); and Giacobini, *Alzheimer Disease: From Molecular Biology to Therapy* eds. Becker et al., pp. 187–204 (1996). Such AChE inhibitors include eptastigmine, metrifonate and phenserine. However, certain AChE inhibitors have limited efficacy, are difficult to titrate, can affect liver function, are contraindicated in many disease states, and can cause side effects (e.g., hepatotoxicity, headache, myalgia, nausea/vomiting, dyspepsia, dizziness, ataxia, anorexia, and diarrhea).

It would be desirable to provide a useful method for the prevention and treatment of a condition or disorder by administering to a patient susceptible to or suffering from such a condition or disorder a therapeutic capable of effecting the ACh level within that patient. It would be highly beneficial to provide individuals suffering from certain disorders (e.g., CNS diseases) with interruption of the symptoms of those disorders by the administration of a pharmaceutical composition containing an active ingredient having nicotinic pharmacology and which has a beneficial effect (e.g., upon the functioning of the CNS), but which does not provide any significant associated side effects. It would be highly desirable to provide a pharmaceutical composition incorporating a compound which interacts with nicotinic receptors, such as those which have the potential to affect the functioning of the CNS, but which compound when employed in an amount sufficient to affect the functioning of the CNS, does not significantly affect those receptor subtypes which have the potential to induce undesirable side effects (e.g., appreciable activity at skeletal muscle and ganglia sites).

SUMMARY OF THE INVENTION

The present invention relates to a method for the prevention or treatment of a variety of conditions or disorders, and particularly those disorders characterized by dysfunction of nicotinic cholinergic neurotransmission. The present invention also relates to a method for the prevention or treatment of disorders, such as central nervous system (CNS) disorders, which are characterized by an alteration in normal neurotransmitter release. The methods involve administering to a subject an effective amount of a pharmaceutical composition of the present invention patients suffering from or susceptible to such disorders. Of particular interest is a method involving the co-administration of (i) at least one nicotinic compound capable of interacting with nicotinic cholinergic receptors (e.g., a nicotinic agonist selective for the α4β2 nicotinic acetylcholine receptor (nAChR) subtype and/or a nicotinic agonist selective for the α4β4 nAChR subtype), and (ii) a component capable of inhibiting the activity of acetylcholinesterase (i.e., an acetylcholinesterase inhibitor). Preferably, the components of an effective dose of the pharmaceutical composition of the present invention includes a combination of submaximal doses of (i) a compound capable of interacting with nicotinic cholinergic receptors (e.g., a nicotinic agonist selective for the α4β2 nicotinic acetylcholine receptor (nAChR) subtype and/or a nicotinic agonist selective for the α4β4 nAChR subtype), and (ii) an AChE inhibitor.

The present invention, in another aspect, relates to a pharmaceutical composition comprising an effective amount of a compound of the present invention. Such a pharmaceutical composition incorporates a compound that has the capability of interacting with relevant nicotinic receptor sites (e.g., a nicotinic agonist), and a compound that is an AChE inhibitor. Such a pharmaceutical composition hence has the capability of acting as a therapeutic agent in the prevention or treatment of a variety of conditions and disorders, particularly those disorders characterized by an alteration in normal neurotransmitter release.

The pharmaceutical compositions of the present invention are useful for the prevention and treatment of CNS disorders. Each pharmaceutical composition provides therapeutic benefit to individuals suffering from certain CNS disorders and exhibiting clinical manifestations of such disorders in that at least one component of that composition has the potential to (i) exhibit nicotinic pharmacology and affect nicotinic receptors sites in the CNS (e.g., act as a pharmacological agonist to activate nicotinic receptors), and (ii) elicit neurotransmitter secretion, and hence prevent and suppress the symptoms associated with those diseases; and at least one component of the composition has the potential to inhibit AChE, the enzyme that hydrolyzes the endogenous neurotransmitter, acetylcholine. In addition, the compounds are expected to have the potential to (i) increase the number of nicotinic cholinergic receptors of the brain of the patient, (ii) exhibit neuroprotective effects and (iii) not provide appreciable adverse side effects associated with the administration of certain levels of nicotinic agonists or AChE inhibitors (e.g., increased heart rate, changes in blood pressure, hepatotoxicity, headache, myalgia, nausea/vomiting, dyspepsia, dizziness, ataxia, anorexia, and diarrhea). The pharmaceutical compositions of the present invention are believed to be safe and effective with regards to prevention and treatment of CNS disorders.

The foregoing and other aspects of the present invention are explained in detail in the detailed description and examples set forth below.

DETAILED DESCRIPTION OF THE INVENTION

Compounds capable of interacting with nicotinic cholinergic receptors can vary. Such compounds exhibit nicotinic pharmacology. Such compounds are selective to nicotinic cholinergic receptors in that such compounds bind with high affinity to relevant receptor subtypes (e.g., those compounds exhibit binding constants of less than 1,000 nM). See, Cheng t al., *Biochem. Pharmacol.* 22: 3099 (1973). Preferably, such compounds are nicotinic agonists. Nicotinic agonists are ligands that activate receptors (i.e., promote opening of ion channels) upon interaction of those ligands with the binding sites of those receptors. See, Bencherif et al., *JPET* 279: 1413–1421 (1996). Nicotinic agonists useful in carrying out the present invention can vary. Such agonists include nicotine and its analogs and derivatives. Exemplary nicotinic agonists are set forth in U.S. Pat. No. 4,965,074 to Leeson; U.S. Pat. No. 5,242,935 to Lippiello et al.; U.S. Pat. Nos. 5,276,043; 5,227,391 to Caldwell et al.; U.S. Pat. No. 5,583,140 to Bencherif et al.; U.S. Pat. No. 5,516,785 to Zoltewicz et al.; PCT WO 96/31475 and European Patent Application No. 588,917. Existing nicotinic agonists providing cognitive benefit are observed to bind to the $α_4β_2$ or $α_4β_4$ nAChR subtypes. See, Bencherif et al., *CNS Drug Review*, 3(4): 325–345 (1998). See, also, Wilkie et al., *Biochem. Soc. Trans.* 21: 429–431 (1993) and Wonnacott et al., In: *Effects of Nicotine on Biological Systems II:* 87–94 (1995).

Certain nicotinic agonists are those that act a ligands at the α4β2 nAChR subtype. Examples of such compounds include those compounds (e.g., heterocyclic ether derivatives) set forth in PCT WO 94/08992 and those compounds (e.g., isoxazole and isothiazole compounds) set forth in PCT WO 92/21339. Especially preferred compounds are aryl substituted amines (e.g., metanicotine, and metanicotine analogs and derivatives), such as those types of compounds set forth in U.S. Pat. No. 5,212,188 to Caldwell et al.; U.S. Pat. No. 5,597,919 to Dull et al.; U.S. Pat. No. 5,616,716 to Dull et al., U.S. Pat. No. 5,663,356 to Ruecroft et al. and U.S. Pat. No. 5,726,316 to Crooks et al.; and U.S. patent application Ser. Nos. 09/054,130 and 09/098,285 the disclosures of which are incorporated herein by reference in their entirety.

Certain nicotinic agonists are those that act a ligands at the α4β4 nAChR subtype. Examples of such compounds include those compounds (e.g., diazabicyclo[3.3.1]nonane derivatives) set forth in PCT WO 96/30372, and those compounds set forth in U.S. Pat. No. 5,242,916 to Lippiello et al. Another example of such a compound is Sibia's SIB-1553A. See, Lloyd et al., *Life Sciences*, 62(17–18):1601–1606 (1998).

Acetylcholinesterase inhibitors useful in carrying out the present invention can vary. Representative acetylcholinesterase inhibitors include galanthamine and analogs thereof (see, U.S. Pat. No. 4,663,318 to Davis, Canadian Patent 2,180,703 and PCT WO 8808708), and those compounds set forth in European Patent Application 411,534 and U.S. Pat. No. 5,231,093 to Flanagan et al., U.S. Pat. No. 5,246,947 to Effland et al. One commercially available ACHR inhibitor Cognex, which is marketed as a treatment for AD as capsule containing tacrine hydrochloride, available from Parke-Davis Division of Warner-Lambert Company. Another commercially available AChE inhibitor is Aricept, which is a capsule containing donezepil hydrochloride, available from Eisai. Other reported AChE inhibitors include Amirine from Nikken Pharmaceuticals, SW-10888 from Sumitomo, MF-217 from Mediolanum Pharmaceutici-Angelini, Ro 45-5934, HP-290 from Hoesht-Russel, ENA 713 from Sandoz, Itameline from Hoesht, Metrifonate from Bayer-Wiles, Tak 177 from Takeda, CP 118.954 from Pfizer, Galanthamine from Naedheim Pharmaceuticals, ONO 1603 from Ono, Zifrosilone from Marion Merrel Dow. See, for example those AChE inhibitors set forth in Brufani et al, *Alzheimer Disease: From Molecular Biology to Therapy*, eds. Becker et al., pp. 171–177 (1996); Schmidt et al., *Alzheimer Disease: From Molecular Biology to Therapy*, eds. Becker et al., pp. 217–221 (1996); Vargas et al., *Alzheimer Disease: From Molecular Biology to Therapy*, eds. Becker et al., pp. 251–255 (1996); Greig et al., *Alzheimer Disease: From Molecular Biology to Therapy*, eds. Becker et al., pp. 231–237 (1996); and Giacobini, *Alzheimer Disease: From Molecular Biology to Therapy* eds. Becker et al., pp. 187–204 (1996). Such AChE inhibitors include eptastigmine, metrifonate and phenserine. Representative AChE inhibitors are set forth in U.S. Pat. Nos. 4,914,102; 5,100,901; 5,102,891; 5,166,181; 5,187,165; 5,288,758; 5,302,593; 5,300,517; 5,338,548; 5,364,864; 5,389,629; 5,391,553; 5,455,245; 5,574,046; 5,602,176; 5,622,976; 5,663,448; 5,693,668 and 5,744,476; European Patent Application Nos. 268,871; 298,202; 409,676; 477,903 and 703,901; and PCT WO 93/13100; 93/16690; 96/40682; 97/19059 and 97/38993, the disclosures of which are incorporated herein by reference in their entirety.

The present invention relates to a method for providing prevention of a condition or disorder to a subject susceptible to such a condition or disorder, and for providing treatment to a subject suffering therefrom. For example, the method comprises administering to a patient an amount of a pharmaceutical composition effective for providing some degree of prevention of the progression of a CNS disorder (i.e., provide protective effects), amelioration of the symptoms of a CNS disorder, and amelioration of the recurrence of a CNS disorder. The method involves administering an effective amount of a pharmaceutical composition.

Pharmaceutical compositions of the present invention are useful for treating those types of conditions and disorders for which other types of nicotinic compounds and AChE inhibitors have been proposed as therapeutics. See, for example, Williams et al. *DN&P* 7(4):205–227 (1994), Arneric et al., *CNS Drug Rev.* 1(1):1–26 (1995), Arneric et al., *Exp. Opin. Invest. Drugs* 5(1):79–100 (1996), Bencherifet al., *JPET* 279:1413 (1996), Lippiello et al., *JPET* 279:1422 (1996), Damaj et al., *Neuroscience* (1997), Holladay et al., *J. Med. Chem* 40(28): 4169–4194 (1997), Bannon et al., *Science* 279: 77–80 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al. CNS disorders which can be treated in accordance with the present invention include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

The pharmaceutical composition also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulants, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, the pharmaceutical composition of the present invention can be employed as part of a formulation with other compounds intended to prevent or treat a particular disorder.

The manner in which the pharmaceutical compositions are administered can vary. Components of those compositions can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebro ventricularly; or transdermally (e.g., using a transdermal patch). Although it is possible to administer the compositions in the form of a bulk active chemical, it is preferred to present each composition in the form of a formulation for efficient and effective administration. Exemplary methods for administering such compositions will be apparent to the skilled artisan. For example, the compositions can be administered in conjunction with a pharmaceutically acceptable carrier, and as such can be administered in the form of a tablet, a hard gelatin capsule or as a time release capsule. As another example, the compositions can be delivered transdermally using the types of patch technologies available from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with receptor sites within the body of the subject that affect the functioning of the CNS. More specifically, in treating a CNS disorder administration preferably is such so as to optimize the effect upon those relevant receptor subtypes which have an effect upon the functioning of the CNS, while minimizing the effects upon muscle-type receptor subtypes. Other suitable methods for administering the compositions of the present invention are described in U.S. Pat. No. 5,604,231 to Smith et al., the disclosure of which is incorporated herein by reference in its entirety.

The appropriate dose of the pharmaceutical composition is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. The effective dose can vary, depending upon factors such as the condition of the patient, the severity of the symptoms of the disorder, and the manner in which the pharmaceutical composition is administered. The effective dose of the composition can differ from patient to patient but in general includes amounts starting where CNS effects or other desired therapeutic effects occur, but below that amount where significant undesirable side effects are observed. Thus, when treating a CNS disorder, an effective amount of composition is an amount sufficient to pass across the blood-brain barrier of the subject; and with regards to one of the components, to bind to relevant receptor sites in the brain of the subject and preferably activate relevant nicotinic receptor subtypes (e.g., provide neurotransmitter secretion, thus resulting in effective prevention or treatment of the disorder); and with regards to the components of the composition, to affect the level of AChE within the brain of the subject. Prevention of the disorder is manifested by delaying the onset of the symptoms of the disorder. Treatment of the disorder is manifested by a decrease in the symptoms associated with the disorder or an amelioration of the recurrence of the symptoms of the disorder.

The present invention involves administering an effective amount of a pharmaceutical composition incorporating (1) an effective amount of any or all of the components of that composition, or (ii) a sub-threshold or submaximal amount of any or all of the components of that composition. A submaximal dose is a dose that is not effective to provide a desired therapeutic effect; that is, a dose that is less than an active dose. Components are employed at submaximal doses (e.g., typically less than 100 percent, often less than 75 percent, frequently less than 50 percent, and even less than 25 percent, of the active dose of that component). Hence, there is provided the potential for minimized side effects associated with any of these compounds at efficacious doses when not employed as a synergistic mixture. However, the components, when used in combination, act between the different pathways to maximize the beneficial effects of these compounds on cognitive functions. That is, even though each component of the pharmaceutical composition is used in amounts that are less than the respective minimal effective doses, the combination of components provides a therapeutic effect.

Typically, the effective dose of the pharmaceutical composition generally requires administering the compound that has the capability of interacting with relevant nicotinic receptor sites (e.g., the nicotinic agonist) in an amount of less than 5 mg/kg of patient weight. Often, such compounds are administered in an amount less than about 1 mg/kg of patient weight, more often less than about 100 ug/kg of patient weight, and frequently between about 1 ug and about 100 ug/kg of patient weight, and preferably between about 5 ug and about 50 ug/kg of patient weight. The foregoing effective doses typically represent that amount administered as a single dose, or as one or more doses administered over a 24 hour period.

The AChE inhibitors are administered in amounts that are dependent upon the particular type of compound employed. See, *Physicians' Desk Reference*. Typically, the effective dose of pharmaceutical composition generally requires administering the AChE inhibitor in an amount of less than about 2 mg/kg of patient weight, when the active ingredient is tacrine hydrochloride; while such amount is less than about 150 ug/kg patient weight, when the active ingredient is donezepil hydrochloride. For example, for tacrine hydrochloride, such amount is less than about 1.5 mg/kg of patient weight, often less than about 1 mg/kg of patient weight, and frequently between about 200 ug and about 800 ug/kg of patient weight, and usually between about 300 ug and about 600 ug/kg of patient weight. For example, for donezepil hydrochloride, such amount is less than about 100 ug/kg of patient weight, often less than about 75 ug/kg of patient weight, and frequently between about 20 ug and about 70 ug/kg of patient weight, and usually between about 30 Mg and about 60 ug/kg of patient weight. The foregoing effective doses typically represent that amount administered as a single dose, or as one or more doses administered over a 24 hour period.

Compositions of the present invention, when employed in effective amounts in accordance with the method of the present invention, are effective towards providing some degree of prevention of the progression of CNS disorders, amelioration of the symptoms of CNS disorders, and amelioration to some degree of the recurrence of CNS disorders. However, such effective amounts of those compositions preferably are not sufficient to elicit any appreciable side effects, as is demonstrated by decreased effects on preparations believed to reflect effects on the cardiovascular system, or effects to skeletal muscle. As such, administration of compositions of the present invention provides a broad therapeutic window in which treatment of certain CNS disorders is effectively provided, and side effects are avoided. That is, an effective dose of a composition of the present invention is sufficient to provide the desired effects upon the CNS, but is preferably insufficient to provide undesirable side effects. Preferably, effective administration of a composition of the present invention resulting in treatment of CNS disorders occurs upon administration of less half that amount sufficient to cause any side effects to a significant degree.

The following examples are provided to illustrate the present invention, and should not be construed as limiting thereof. In these examples, all parts and percentages are by weight, unless otherwise noted.

EXAMPLE 1

A nicotinic agonist selective to an nAChR subtype is (2S)-(4E)-N-methyl-5-(5-isopropoxy-3-pyridyl)-4-penten-2-amine hemigalactarate, which was prepared in accordance with the following techniques:

(2R)-4-Penten-2-ol (2R)-4-Penten-2-ol was prepared in 82.5% yield from (R)-(+)-propylene oxide according to procedures set forth in A. Kalivretenos, J. K. Stille, and L. S. Hegedus, *J. Org. Chem.* 56: 2883 (1991).

(2R)-(4E)-5-(5-Isopropoxy-3-pyridyl)-4-penten-2-ol

A mixture of 5-bromo-3-isopropoxypyridine (10.26 g, 47.50 mmol), (2R)-4-penten-2-ol (4.91 g, 57.00 mmol), palladium(II) acetate (106 mg, 0.47 mmol), tri-o-tolylphosphine (578 mg, 1.90 mmol), triethylamine (28.46 mL, 204.25 mmol), and acetonitrile (30 mL) were heated in a sealed glass tube at 140° C. for 14 h. The reaction mixture was cooled to ambient temperature, diluted with water, and extracted with chloroform (3×200 mL). The combined chloroform extracts were dried over sodium sulfate, filtered, and concentrated by rotary evaporation to give a pale-yellow oil (8.92 g, 85.0%).

(2R)-(4E)-5-(5-Isopropoxy-3-pyridyl)-4-penten-2-ol p-Toluenesulfonate

To a stirred solution of (2R)-(4E)-5-(5-isopropoxy-3-pyridyl)-4-penten-2-ol (8.50 g, 38.46 mmol) in dry pyridine (30 mL) at 0° C. was added p-toluenesulfonyl chloride (14.67 g, 76.92 mmol). The reaction mixture was stirred for 24 h at ambient temperature. The pyridine was removed by rotary evaporation. Toluene (50 mL) was added to the residue and removed by rotary evaporation. The crude product was stirred with a saturated solution of sodium bicarbonate (100 mL) and extracted with chloroform (3×100 mL). The combined chloroform extracts were dried over sodium sulfate, filtered, and concentrated by rotary evaporation to yield a dark-brown, viscous oil (11.75 g, 81.5%).

(2S)-(4E)-N-Methyl-5-(5-isopropoxy-3-pyridyl)-4-penten-2-amine

A mixture of (2R)-(4E)-5-(5-isopropoxy-3-pyridyl)-4-penten-2-ol ptoluenesulfonate (11.00 g, 29.33 mmol), methylamine (200 mL, 40% solution in water), and ethyl alcohol (10 mL) was stirred at ambient temperature for 18 h. The resulting solution was extracted with chloroform (3×100 mL). The combined chloroform extracts were dried over sodium sulfate, filtered, and concentrated by rotary evaporation. The crude product was purified by column chromatography over aluminum oxide, eluting with ethyl acetate-methanol (7:3, v/v). Selected fractions were combined and concentrated by rotary evaporation, producing an oil. Further purification by vacuum distillation furnished 2.10 g (31.0%) of a colorless oil, bp 90–100° C. at 0.5 mm Hg.

(2S)-(4E)-N-Methyl-5-(5-isopropoxy-3-pyridyl)-4-penten-2-amine Hemigalactarate (2S)-(4E)-N-Methyl-5-(5-isopropoxy-3-pyridyl)-4-penten-2-amine (2.00 g, 8.55 mmol) was dissolved in ethyl alcohol (20 mL), assisted by warming to 70° C. The warm solution was treated with galactaric acid (900 mg, 4.27 mmol) in one portion, followed by the dropwise addition of water (0.5 mL). The solution was filtered while hot to remove some insoluble material. The filtrate was allowed to cool to ambient temperature. The resulting crystals were filtered, washed with anhydrous diethyl ether, and dried under vacuum at 40° C. to yield a white, crystalline powder (750 mg, 26.0%), mp 140–143° C.

An AChE inhibitor, tacrine, is commercially available as Cognex. Caplets containing 40 mg of active ingredient were used for carrying out the present example.

A step-through passive avoidance paradigm is a test is designed to assess the ability of a compound to reverse scopolamine-induced amnesia in rats. A positive outcome in this paradigm supports the notion that the tested compound has potential cognition enhancing effects, an end-point relevant to some CNS disorders. Briefly, a Gemini Avoidance System (San Diego Instruments) was used for these experiments. During the period of habituation, rats received a subcutaneous injection of saline. On the acquisition day, each rat received a subcutaneous injection of 0.5 μmol/kg scopolamine (or saline in the case of the vehicle control group) 30 minutes prior to being placed in the chambers. Five minutes following scopolamine injection, (or twenty-five minutes before being placed in the chamber), each rat was administered a subcutaneous injection with one of four doses of the pharmaceutical composition component ingredients. Thirty minutes following the scopolamine or vehicle injection, each rat was placed in the brightly illuminated chamber, facing away from the sliding door. After ten seconds, the door separating the chambers opened allowing access to the dark chamber. The time to enter the dark chamber was measured. Immediately upon entering the dark chamber, the rat received a mild foot-shock (0.5 mAmp) for 2 second duration. Twenty-four hours following training, each rat was placed in the light chamber facing away from the sliding door. Thirty seconds later the door was opened and the rat was allowed to enter the dark chamber. Upon entering the dark chamber the sliding door was closed and the rat was removed from the apparatus (no shock was delivered). If the rat did not enter the dark chamber within 300 seconds, a ceiling score of 300 seconds was recorded for that rat, and the rat was removed from the apparatus and returned to its home cage. Following saline sub-cutaneous injection, animals were not cognitively impaired and did not enter the avoidance chamber. The latency was markedly longer (>70 seconds, on average) than those rendered amnesic with scopolamine (latency of less than 10 seconds, on average). Following treatment with tacrine at 1.2, 4, and 12 μmol/kg; the latency was unchanged at 1.2 mmol/kg (not significantly different than scopolamine), and was increased to 30 and 25 seconds, at 4 and 12 μmol/kg, respectively. Following treatment with (2S)-(4E)-N-methyl-5-(5-isopropoxy-3-pyridyl)-4-penten-2-amine at 0.6, 1 and 3 μmol/kg, the latency increased to approximately 25, 55 and 20 seconds, respectively. The co-administered combination of tacrine (1.2 pmol/kg) and (2S)-(4E)-N-methyl-5-(5-isopropoxy-3-pyridyl)-4-penten-2-amine (0.6 μmol/kg) resulted in increased latency to 40 seconds, which was greater than either component alone. Further, the co-administered combination provided increased latency at a submaximal dose of tacrine.

The foregoing is illustrative of the present invention and is not to be construed as limiting thereof. The invention is defined by the following claims, with equivalents of the claims to be included therein.

That which is claimed is:

1. A pharmaceutical composition comprising a pharmaceutically effective amount of at least two components, the first component being a nicotinic agonist possessing selectivity to at least one nicotinic receptor subtype selected from the group consisting of an α4β2 nicotinic receptor subtype and an α4β4 nicotinic receptor subtype and the second component being an acetylcholinesterase inhibitor, wherein the first component is present in an amount between about 5 μg and about 50 μg/kg of patient weight and wherein the second component is present in an amount between about 30 μg and about 600 μg/kg of patient weight.

2. A composition of claim 1 wherein the nicotinic agonist is an aryl substituted amine.

3. A composition of claim 1 wherein the nicotinic agonist is E-metanicotine.

4. A composition of claim 1 wherein the nicotinic agonist is (2S)-(4E)-N-methyl-5-(5-isopropoxy-3-pyridyl)-4-penten-2-amine.

5. The composition of claim 1 wherein the acetylcholinesterase inhibitor is tacrine.

6. A method for treating CNS disorders comprising administering to a subject a pharmaceutically effective amount of a pharmaceutical composition incorporating a nicotinic agonist possessing selectivity to at least one nicotinic receptor subtype selected from the group consisting of an α4β2 nicotinic receptor subtype and an α4β4 nicotinic receptor subtype and an acetylcholinesterase inhibitor, wherein the nicotinic agonist is administered in an amount between about 5 μg and about 50 μg/kg of patient weight and wherein the acetylcholinesterase inhibitor is administered in an amount between about 30 μg and about 600 μg/kg of patient weight.

7. The method of claim 6 wherein the nicotinic agonist is an aryl substituted amine.

8. The method of claim 6 wherein the nicotinic agonist is E-metanicotine.

9. The method of claim 6 wherein the nicotinic agonist is (2S)-(4E)-N-methyl-5-(5-isopropoxy-3-pyridyl)-4-penten-2-amine.

10. The method of claim 6 wherein the acetylcholinesterase inhibitor is tacrine.

* * * * *